(12) United States Patent
Lichtenberg et al.

(10) Patent No.: US 6,362,370 B1
(45) Date of Patent: *Mar. 26, 2002

(54) WOOD PRESERVATIVES

(75) Inventors: Florian Lichtenberg, Grenzach; Joachim Fritschi, Lorrach; Volker Ranft, Murg, all of (DE)

(73) Assignee: Lonza AG (CH)

( * ) Notice: Subject to any disclaimer, the term of this patent is extended or adjusted under 35 U.S.C. 154(b) by 0 days.

This patent is subject to a terminal disclaimer.

(21) Appl. No.: 09/656,505

(22) Filed: Sep. 6, 2000

Related U.S. Application Data

(62) Division of application No. 09/194,603, filed as application No. PCT/EP97/02633 on May 22, 1997, now Pat. No. 6,180,672.

(30) Foreign Application Priority Data

May 28, 1996 (CH) ................................................ 1326/96

(51) Int. Cl.⁷ ............................................. C07C 211/63
(52) U.S. Cl. ..................... 564/281; 564/285; 564/291; 564/292; 564/294; 514/561; 514/499; 514/558; 514/642; 514/643; 514/663; 106/18; 106/18.32; 106/18.33; 252/400.62; 252/404; 424/DIG. 11; 424/630; 424/631; 424/638; 504/345
(58) Field of Search ................................. 564/281, 285, 564/292, 294; 514/561, 499, 558, 642, 643, 663; 106/18, 18.32, 18.33; 252/400.62, 404; 424/DIG. 11, 630, 631, 638; 504/345

(56) References Cited

U.S. PATENT DOCUMENTS 5,076,828 A * 12/1991 Taniuchi et al. ................ 71/86
6,180,672 B1 * 1/2001 Lichtenberg et al. ......... 514/86

* cited by examiner

Primary Examiner—Shailendra Kumar
(74) Attorney, Agent, or Firm—Fisher, Christen & Sabol

(57) ABSTRACT

Wood preservatives having biocidal properties which include quaternary ammonium compounds of general formula (I):

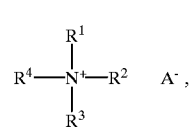

wherein $R^1$ is a $C_{8-18}$-alkyl group or an optionally substituted benzyl group, $R^2$ is a $C_{8-18}$-alkyl group, $R^3$ is a $C_{1-4}$-alkyl group or a group of the formula $-[CH_2-CH_2-O]_n-H$, $R^4$ is a $C_{1-4}$-alkyl group, n is a number from 0.5 to 8, preferably from 1 to 5, and $A^{31}$ is the anion of an organic carboxylic acid which contains 2 to 12 C atoms and carries at least one hydroxyl, amino or sulfonic acid group. The wood preservatives also penetrate deeply into the wood without the use of pressure, and have only a mild corrosive action on metals. Furthermore, a process for treating timbers with these compositions, concentrates for the preparation thereof, the use of new and known quaternary ammonium compounds in wood preservatives and new quaternary ammonium compounds and their use as biocides.

5 Claims, No Drawings

WOOD PRESERVATIVES

This application is a division of U.S. Ser. No. 09/194,603, filed on Jul. 6, 1999, now U.S. Pat. No. 6,180,672, which is a 371, PCT/EP97/02633 filed May 22, 1997.

The present invention relates to wood preservatives based on quaternary ammonium compounds, a process for treating timbers with these compositions, concentrates for the preparation thereof, the use of new and known quaternary ammonium compounds in wood preservatives, and new quaternary ammonium compounds and their use as biocides.

The biocidal properties of quaternary ammonium compounds (QAC), in particular their activity against fungi and bacteria, are generally known. Corresponding references can be traced back to the start of the nineteen thirties. A particular property of QAC is their ability to add relatively firmly on to the most diverse substrate surfaces, because of their charge and surface activity. This addition is also decisive for the duration of their action, for example in the field of surface disinfection. However, this property is a disadvantage if QAC solutions are to penetrate deeply into a porous substrate, such as, for example, wood. In this case, the desired deep action is prevented by the rapid and complete absorption in the region close to the surface. This is also a reason why QAC are employed comparatively little in wood preservatives, especially if the wood preservatives are those which are to be applied in a process without pressure, such as dipping, trough impregnation, flooding, brushing or spraying. However, because of their toxicological acceptability compared with other wood preservatives, the use of QAC would be desirable precisely in the indoor area.

The object of the present invention was therefore to provide a wood preservative based on quaternary ammonium compounds which also penetrates easily and deeply into wood or other porous substrates without the use of pressure.

This object is achieved according to the invention by the wood preservative according to invention.

It has been found, surprisingly, that the penetration depth and the distribution of the active compound in wood and wood materials, and also in other porous substrates, are influenced substantially by the properties of the anion. QAC are usually employed in the form of the chlorides and bromides, which is chiefly due to the nature of their preparation. Some QAC which contain anions of simple aliphatic carboxylic acids, such as acetate or propionate, are also known. Surprisingly, the penetration capacity of QAC increases to a significant extent if, instead of anions of unsubstituted carboxylic acids, anions of low molecular weight carboxylic acids having from 2 to 12 carbon atoms which also carry, in addition to the carboxyl group, at least one hydroxyl group, amino group or sulphonic acid group (sulpho group) are employed. These carboxylic acids can be aliphatic (linear or branched), alicyclic or aromatic in this case. The quaternary ammonium compounds according to the invention can be represented by the general formula

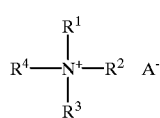

I

In this formula: $R^1$ is a $C_{8-18}$-alkyl group or an optionally substituted benzyl group, $R^2$ is a $C_{8-18}$-alkyl group, $R^3$ is a $C_{1-4}$-alkyl group or a group of the formula —[$CH_2$—$CH_2$—O]$_n$—H, $R^4$ is a $C_{1-4}$-alkyl group, n is a number from (as a statistical average) 0.5 to 8, preferably 1 to 5, and $A^-$ is the anion of an organic carboxylic acid which contains 2 to 12 carbon atoms and carries at least one hydroxyl, amino or sulphonic acid group.

$C_{m-n}$-alkyl groups are to be understood as meaning linear or branched alkyl groups having m to n carbon atoms. In this connection, $C_{8-18}$-alkyl is also to be understood as the mixtures of different chain lengths obtainable from natural sources, such an, for example, coconut fatty acid, in which small contents of unsaturated radicals or traces of shorter- or longer-chain radicals can optionally be present. Examples of suitable substituents of the benzyl group are halogen (preferably chloro), $C_{1-4}$-alkyl (preferably methyl), $C_{1-4}$-alkoxy (preferably methoxy), hydroxy, amino, $C_{1-4}$-alkyl amino (preferably methylamino) and di($C_{1-4}$-alkyl)amino (preferably diethylamino). One or more of such substituents are possible, which can be the same or different.

Organic carboxylic acids containing 2 to 12 carbon atoms which carry at least one hydroxyl, amino or sulphonic acid group are to be understood as meaning both aliphatic or cycloaliphatic and aromatic carboxylic acids. Carboxylic acids which carry one hydroxyl or amino group are preferred. Lactic acid or the lactate ion, hydroxyacetic acid (glycolic acid) or the hydroxyacetate ion, simple amino acids, such as aminoacetic acid (glycine) or the aminoacetate ion (glycinate ion), α- and β-alanine or the 2-amino- and the 3-aminopropionate ion, and o-, m- and p-hydroxybenzoic acid or the corresponding hydroxybenzoate ions are particularly preferred. These anions have proved to be particularly active in the context of the invention.

Particularly preferred cations are N,N-dimethyl-N-benzyl-N-(coconut alkyl)ammonium, N,N-didecyl-N-methyl-N-(polyoxyethyl)ammonium or N,N-didecyl-N,N-dimethyl-ammonium.

N,N-Di-$C_{8-12}$-alkyl-N—$C_{1-4}$-alkyl-N-(polyoxyethyl) ammonium salts are known compounds and are accessible by a process described in DE-A 33 19 509. The other QAC which can be employed according to the invention can be prepared from the corresponding chlorides by a method described in WO-A 94/28715 (pages 13–14), analogously to the compounds disclosed therein. The chlorides are known compounds and are commercially obtainable in some cases.

The wood preservatives according to the invention can also comprise the QAC equipped with corresponding anions in combination with one or more additional biocides. Suitable additional biocides are, for example:

Amphosurfactants having a biocidal action,
Methyl benzimidazole-2-carbamate,
1,2-Benzisothiazol-3-one,
Biguanides having a biocidal action,
Organic and inorganic boron compounds,
α-tert-Butyl-α-(p-chlorophenethyl)-1H-1,2,4-triazole-1-ethanol,
(2-sec-Butylphenyl)N-methylcarbamate,
(+)-cis-4-[3-(tert-Butylphenyl)-2-methylpropyl]-2,6-dimethylmorpholine,
5-Chloro-2-methyl-4-isothiazolin-3-one,
1-(6-Chloro-3-pyridinyl)-methyl-4,5-dihydro-N-nitro-1H-imidazol-2-amine,
Chlorohexidine and salts thereof,
Chlorinated phenols, such as tetra- and pentachlorophenol,
Chloronitrobenzene derivatives,
1-(4-Chlorophenyl)-3-(2,6-difluorobenzoyl)-urea, N-Cyclohexyl-N-methoxy-2,5-dimethylfuran-3-carboxamide,
Di-(guanidino-octyl)-amine,
Cyano-(3-phenoxyphenyl)methyl 2,4-dichloro-α-(1-methylethyl)-phenylacetate,
Cyano-(3-phenoxyphenyl)methyl 4-chloro-α-(1-methylethyl)-phenylacetate(fenvalerate),
α-[2-(4-Chlorophenyl)-ethyl]-α-(1,1-dimethylethyl)-1H-1,2,4-triazole-1-ethanol,
Cyano-(4-fluoro-3-phenoxyphenyl)methyl 3-(2,2-dichloroethenyl)-2,2-dimethylcyclopropane-1-carboxylate,
Cyano-(3-phenoxyphenyl)methyl (1R,3R)-3-(2,2-dibromoethenyl)-2,2-dimethylcyclopropane-1-carboxylate(deltamethrin),
Cyano-(3-phenoxyphenyl)methyl 3-(2,2-dichloroethenyl)-2,2-dimethylcyclopropane-1-carboxylate (cypermethrin),
3-Phenoxyphenyl)methyl 3-(2,2-dichloroethenyl)-2,2-dimethylcyclopropane-1-carboxylate(permethrin),
1-{[2-(2,4-Dichlorophenyl)-1,3-dioxolan-2-yl]methyl}-1H-1,2,4-triazole,
1-{[2-(2,4-Dichlorophenyl)-4-propyl-1,3-dioxolan-2-yl]methyl}-1H-1,2,4-triazole,
O,O-Diethyl O-(α-cyanobenzylideneamino)thiophosphate(phoxim),
O,O-Diethyl O-(3,5,6-trichloro-2-pyridyl)thionophosphate(chlorpyriphos),
O,O-Diethyl S-(6-chloro-2,3-dihydro-2-oxobenzoxazol-3-yl)methyl dithiophosphate(phosalone),
O,O-Dimethyl S-[2-(methylamino)-2-oxoethyl]dithiophosphate(dimethoate),
O,O-Dimethyl S—(N-phthalimidomethyl)dithiophosphate(phosmet),
N,N-Dimethyl-N'-phenyl-N'-(fluoromethylthio)sulphamide,
N,N-Dimethyl-N'-tolyl-N'-(fluoromethylthio)sulphamide,
3,5-Dimethyltetrahydro-1,3,5-thiadiazine-2-thione,
Dimethylalkylamine salts,
Dithiocarbamates (metal and amine salts),
2-(2-Furanyl)-1H-benzimidazole,
Halogenoacetic acids and amides and esters thereof,
6,7,8,9,10,10-Hexachloro-1,5,5a,6,9,9a-hexahydro-6,9-methano-2,4,3-benzodioxathiepine 3-oxide (endosulfan),
Hexachlorocyclohexane,
8-Hydroxyquinoline, the copper salt thereof and halogenated derivatives thereof,
2-Iodobenzoanilide,
1-Naphthyl N-methylcarbamate,
2-Methyl-4-isothiazolin-3-one,
Methylene bisthiocyanate,
Nitroalkanols having biocidal action,
N-Nitroso-N-cyclohexylhydroxylamine and salts thereof,
N-Nitroso-N-phenylhydroxylamine and salts thereof,
2-N-Octyl-4-isothiazoline-3-one,
Organotin compounds, such as, for example, tributyltin oxide and tributyltin benzoate,
Phenylphenols, (2-Isopropoxyphenyl)N-methylcarbamate,
Pyridine-2-thiol 1-oxide and salts thereof,
Salicylanilide and halogenated derivatives thereof,
Tetrachloroisophthalodinitrile,
2-(Thiazol-4-yl)-benzimidazole,
2-(Thiocyanomethyl)-thiobenzothiazole,
1-(1,2,4-Triazol-1-yl)-1-(4-chlorophenoxy)-3,3-dimethylbutan-2-ol,
1-(1,2,4-Triazol-1-yl)-1-(4-chlorophenoxy)-3,3-dimethylbutan-2-one,
N-(1,1,2,2-Tetrachloroethylthio)-3,6,7,8-tetrahydrophthalimide,
N-(Trichloromethylthio )-3,6,7,8-tetrahydrophthalimide,
N-(Trichloromethylthio)phthalimide,
N-Tridecyl-2,6-dimethylmorpholine.

Particularly preferred additional biocides are copper compounds and zinc compounds.

The wood preservatives according to the invention are advantageously prepared and transported as concentrates having a content of 5–90% by weight of the quaternary ammonium compound (I).

These concentrates comprise water as the solvent and, if appropriate, other solvents and/or other biocides or auxiliaries. The other solvents include, for example, water-miscible solvents, such as lower alcohols and glycols, and esters and ethers thereof, which are used as solubilizing agents and/or to lower the freezing point. Auxiliaries which can be employed are, for example, defoamers, antioxidants, dyestuffs or fragrances.

The wood preservatives according to the invention are advantageously used in a 2–20% strength aqueous solution of the concentrates, corresponding to a QAC concentration of 0.1–10%, and in particular preferably by trough impregnation. The wood to be preserved is stored in the solution for some hours to days. After absorption of 20–80 g of concentrate per square metre of wood surface, permanent protection against wood-destroying organisms is achieved, in particular against higher fungi from the sub-classes Ascomycetes (asco fungi) and Basidiomycetes, wood-discolouring fungi (blue stain fungi) and wood-destroying insects, such as Anobium species or the longhorn beetle. Wood protected in this way complies with the requirements of hazard classes 1 to 3 in accordance with DIN 68 800 Part 3 and EN 599 and is suitable both for the indoor and for the outdoor area.

Surprisingly, it has been found that the penetration-ready QAC according to the invention are suitable for also transporting other biocidal active compounds deep into the substrate, so that these QAC, in particular the lactate and the hydroxy acetate, for example, are also suitable as entraining agents in the biocidal treatment of leather.

The QAC according to the invention show further advantageous and in some cases unexpected properties during formulation.

The lactates, hydroxyacetates and hydroxybenzoates show a relatively high compatibility with other substances in the formulation, for example with dyestuffs, pigments, waxes and the like.

The corrosive action, in particular on iron and iron alloys, of the QAC according to the invention is lower than in the case of the corresponding halides by a factor of 5–10.

It has been found, completely unexpectedly, that the biological action is higher than could be expected on the basis of the knowledge of conventional QAC with a halide anion.

The following examples are intended to describe the nature of the formulation of the wood and material preservatives according to the invention in more detail. The recipe for the concentrate is given in each case. All data are in percentages by weight in each case.

EXAMPLE 1

Wood preservative for immersion treatment of structural wood

20% of N,N-didecyl-N,N-dimethylammonium hydroxyacetate

80% of water

EXAMPLE 2

Wood preservative for dipping treatment of structural wood in the tropics

40% of N,N-didecyl-N-methyl-N-(polyoxyethyl)ammonium lactate

10% of diethylene glycol monobutyl ether

50% of water

EXAMPLE 3

Deep preservative for wood in the outdoor area

20% of N,N-didecyl-N-methyl-N-(polyoxyethyl)ammonium lactate

10% of copper hydroxycarbonate

40% of monoethanolamine

30% of water

EXAMPLE 4

Deep preservative for wood in the outdoor area

25% of N,N-didecyl-N-methyl-N-(polyoxyethyl)ammonium hydroxyacetate

10% of zinc acetate, anhydrous

20% of diethanolamine

2% of o-phenylphenol

43% of water

The depth of penetration in the wood in the examples mentioned is 5–10 mm, so that comprehensive deep preservation is ensured.

EXAMPLES 5–9

Comparison Examples V1–V4

The following table 1 shows, by way of example, how the replacement of the halide ions by anions of simple carboxylic acids (acetate, propionate; not according to the invention) or, according to the invention, by anions of hydroxy- or aminocarboxylic acids has an effect.

The QAC used in this example were the N,N-dimethyl-N-benzyl-N-(coconut alkyl)ammonium cation (I) and the N,N-didecyl-N-methyl-N-(polyoxyethyl)ammonium cation (II).

Fine sapwood blocks of dimensions 2.5 cm×5.0 cm×12 cm were impregnated with the QAC shown in the table by immersion in an aqueous solution of in each case 5% strength. The immersion time was a standard 24 hours (at 20° C.).

TABLE 1

| Example No. | Cation | Anion | Penetration depth [mm] |
|---|---|---|---|
| V1 | I | Chloride | 1–3 |
| V2 | I | Acetate | 2–3 |
| 5 | I | Lactate | 6–8 |
| 6 | I | Hydroxyacetate (glycolate) | 7–8 |
| V3 | II | Chloride | 2–3 |
| V4 | II | Propionate | 3–4 |
| 7 | II | Lactate | 7–8 |
| 8 | II | Hydroxyacetate (glycolate) | 7–10 |
| 9 | II | Aminoacetate (glycinate) | 6–8 |

The results clearly show that, for example, the lactate and the hydroxyacetate (glycolate) are particularly suitable for formulation and preparation of wood preservatives.

EXAMPLES 10–11

Comparison Examples V5–V7

Bars of beechwood (1 cm×1 cm×40 cm) were impregnated by immersion in a 0.5% strength solution of the SAC for 24 hours and then tested by the soil burying method according to Schwammkeller. For this, treated and untreated timbers were buried in fungus-infested soil (forest soil). The service life here is defined as the time after which the flexural breaking strength has fallen to 25% of the initial value of (untreated) comparison timbers of the same dimensions and type of wood. The results are summarized in the following Table 2.

TABLE 2

| Example No. | Cation | Anion | Service life [months] |
|---|---|---|---|
| V5 | I | Chloride | 3 |
| 10 | I | Lactate | >9 |
| V6 | II | Chloride | 4 |
| 11 | II | Lactate | >9 |
| V7 | Control (untreated) | — | ~2 |

What is claimed is:

1. A concentrate for the preparation of a wood preservative comprising 5 to 90 percent by weight of a quaternary ammonium compound of the formula:

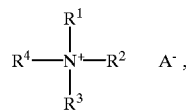

$$R^4-N^+ \begin{array}{c} R^1 \\ | \\ | \\ R^3 \end{array} R^2 \quad A^-, \qquad I$$

wherein $R^1$ is a $C_{8-18}$-alkyl group or an optionally substituted benzyl group, $R^2$ is a $C_{1-4}$-alkyl group, $R^3$ is a $C_{1-4}$-alkyl group or a group of the formula —[CH$_2$—CH$_2$—O]$_n$—H, $R^4$ is a $C_{1-4}$-alkyl group, n is a number from 0.5 to 8, and $A^-$ is the anion of an organic monocarboxylic acid which contains 2 to 12 C atoms and carries at least one hydroxyl, amino or sulfonic acid group, and water, one or more other biocides and/or one or more auxiliaries from the group consisting of defoamers, antioxidants, dyestuffs and fragrances, and, optionally, one or more water-miscible organic solvents.

2. A concentrate for the preparation of a wood preservative, comprising 5 to 90 percent by weight of a quaternary ammonium compound of the formula:

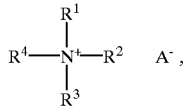

wherein $R^1$ is a $C_{8-18}$-alkyl group or an optionally substituted benzyl group, $R^2$ is a $C_{1-4}$-alkyl group, $R^4$ is a $C_{1-4}$-alkyl group, n is a number from 0.5 to 8, $A^-$ is aminoacetate, 2-aminopropionate, 3-aminopropionate, o-hydroxybenzoate, m-hydroxybenzoate or p-hydroxybenzoate and $R^3$ is a $C_{1-4}$-alkyl group.

3. Quaternary ammonium compound of the formula:

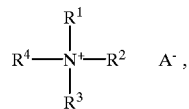

wherein $R^1$ is a $C_{8-18}$-alkyl group or an optionally substituted benzyl group, $R^2$ is a $C_{1-4}$-alkyl group, $R^4$ is a $C_{1-4}$-alkyl group, n is a number from 0.5 to 8, $A^-$ is aminoacetate, 2-aminopropionate, 3-aminopropionate, o-hydroxybenzoate, m-hydroxybenzoate or p-hydroxybenzoate and $R^3$ is a $C_{1-4}$-alkyl group.

4. The quaternary ammonium compound according to claim 3, wherein $R^1$ is a $C_{8-14}$-alkyl group, a coconut alkyl group or a benzyl group and $R^2$ is a $C_{8-14}$-alkyl group or a coconut alkyl group and $R^3$ and $R^4$ are methyl groups.

5. The quaternary ammonium compound according to claim 4, wherein $R^1$ is a benzyl group and $R^2$ is a coconut alkyl group.

* * * * *